United States Patent
Brown et al.

(10) Patent No.: US 11,837,343 B2
(45) Date of Patent: *Dec. 5, 2023

(54) IDENTIFYING REPETITIVE PORTIONS OF CLINICAL NOTES AND GENERATING SUMMARIES PERTINENT TO TREATMENT OF A PATIENT BASED ON THE IDENTIFIED REPETITIVE PORTIONS

(71) Applicant: Merative US L.P., Ann Arbor, MI (US)

(72) Inventors: Eric W. Brown, New Fairfield, CT (US); Maria Eleftheriou, Mount Kisco, NY (US); Anca Sailer, Scarsdale, NY (US); Ching-Huei Tsou, Briarcliff Manor, NY (US)

( * ) Notice: Subject to any disclaimer, the term of this patent is extended or adjusted under 35 U.S.C. 154(b) by 1043 days.

This patent is subject to a terminal disclaimer.

(21) Appl. No.: 15/966,347

(22) Filed: Apr. 30, 2018

(65) Prior Publication Data

US 2019/0333611 A1  Oct. 31, 2019

(51) Int. Cl.
*G06Q 50/00* (2012.01)
*G16H 10/60* (2018.01)
(Continued)

(52) U.S. Cl.
CPC ........... *G16H 10/60* (2018.01); *G06F 16/313* (2019.01); *G06N 20/00* (2019.01); *G16H 50/20* (2018.01)

(58) Field of Classification Search
CPC ...... G16H 10/60; G16H 50/20; G06F 16/313; G06N 20/00
See application file for complete search history.

(56) References Cited

U.S. PATENT DOCUMENTS

| 8,275,803 B2 | 9/2012 | Brown et al. |
| 9,690,861 B2 | 6/2017 | Boloor et al. |

(Continued)

OTHER PUBLICATIONS

Denny, Joshua C. et al., "Evaluation of a Method to Identify and Categorize Section Headers in Clinical Documents", Journal of the American Medical Informatics Association, Nov. 1, 2009, pp. 806-815.

(Continued)

*Primary Examiner* — Rajesh Khattar
(74) *Attorney, Agent, or Firm* — Stephen J. Walder, Jr.

(57) ABSTRACT

A mechanism is provided in a data processing system comprising a processor and a memory, the memory comprising instructions that are executed by the processor to specifically configure the processor to implement a repetitive portion identification and weighting engine. A machine learning model is trained for weighting repetitive portions of patient electronic medical records (EMRs). A repetitive portion identification component applies a plurality of templates to clinical notes of a patient EMR to identify one or more candidate portions that match at least one of the plurality of templates. A content analysis component performs content analysis on the one or more candidate portions to determine whether each given candidate portion is relevant. A weighting component assigns a relative weight to each given candidate portion based on relevance. A cognitive summary graphical user interface (GUI) generation component generates cognitive summary reflecting at least a subset of the one or more candidate portions of the patient EMR. The mechanism outputs the cognitive summary in a GUI to a user.

18 Claims, 5 Drawing Sheets

(51) Int. Cl.
  *G06F 16/31* (2019.01)
  *G06N 20/00* (2019.01)
  *G16H 50/20* (2018.01)

(56) References Cited

U.S. PATENT DOCUMENTS

| | | | |
|---|---|---|---|
| 9,715,576 B2 | 7/2017 | Hayter, II | |
| 2004/0172294 A1* | 9/2004 | Dahlin | G16H 40/20 705/2 |
| 2009/0287678 A1 | 11/2009 | Brown et al. | |
| 2010/0145720 A1* | 6/2010 | Reiner | G16Z 99/00 705/2 |
| 2010/0223226 A1* | 9/2010 | Alba | G06Q 30/02 706/55 |
| 2011/0066587 A1 | 3/2011 | Ferrucci et al. | |
| 2011/0125734 A1 | 5/2011 | Duboue et al. | |
| 2012/0215560 A1 | 8/2012 | Ofek et al. | |
| 2013/0007055 A1 | 1/2013 | Brown et al. | |
| 2013/0018652 A1 | 1/2013 | Ferrucci et al. | |
| 2013/0066886 A1 | 3/2013 | Bagchi et al. | |
| 2013/0317848 A1 | 11/2013 | Savin | |
| 2014/0350961 A1* | 11/2014 | Csurka | G16H 10/60 705/3 |
| 2014/0365210 A1* | 12/2014 | Riskin | G06F 40/103 704/9 |
| 2015/0025909 A1 | 1/2015 | Hayter, II | |
| 2016/0019299 A1* | 1/2016 | Boloor | G06F 16/36 705/3 |
| 2016/0092433 A1* | 3/2016 | Gluck | G06F 40/166 715/256 |
| 2016/0110343 A1* | 4/2016 | Kumar Rangarajan Sridhar | G06F 40/216 704/9 |
| 2017/0161613 A1* | 6/2017 | Dubey | G06F 16/24575 |
| 2017/0193185 A1* | 7/2017 | Barker | G06F 16/334 |
| 2017/0300635 A1* | 10/2017 | Ganesan | G16H 15/00 |
| 2017/0351830 A1* | 12/2017 | Burger | G16H 80/00 |

OTHER PUBLICATIONS

List of IBM Patents or Patent Applications Treated as Related, Dec. 7, 2018, 2 pages.

"The Era of Cognitive Systems: An inside look at IBM Watson and how it works", IBM Corporation, IBM Software Group, Whitepaper, IBM Watson Solutions, Sep. 2012, 19 pages.

Abedtash, Hamed, "An Interoperable Electronic Medical Record-Based Platform for Personalized Predictive Analytics", Indiana University-Purdue University Indianapolis (IUPUI), Doctor of Philosophy in the School of Informatics and Computing, Doctoral Dissertation, Jul. 2017, 184 pages.

Alemzadeh, Homa et al., "An NLP-based Cognitive System for Disease Status Identification in Electronic Health Records", IEEE, 2017 IEEE EMBS International Conference on Biomedical & Health Informatics (BHI), Feb. 16-19, 2017, 4 pages.

Deleger, Louise et al., "Building Gold Standard Corpora for Medical Natural Language Processing Tasks", American Medical Informatics Association, AMIA Annual Symposium Proceedings, vol. 2012, Nov. 3, 2012, pp. 144-153.

Demner-Fushman, Dina et al., "What can Natural Language Processing do for Clinical Decision Support?", National Institutes of Health, Author Manuscript, J Biomed Inform., vol. 42, No. 5, Oct. 2009, pp. 760-772.

High, Rob, "The Era of Cognitive Systems: An Inside Look at IBM Watson and How it Works", IBM Corporation, Redbooks, Dec. 12, 2012, 16 pages.

McCord, M.C. et al., "Deep parsing in Watson", IBM J. Res. & Dev. vol. 56 No. 3/4 Paper 3, May/Jul. 2012, pp. 3:1-3:15.

Perer, Adam et al., "Mining and exploring care pathways from electronic medical records with visual analytics", Elsevier Inc., Journal of Biomedical Informatics, vol. 56, Jul. 2, 2015, pp. 369-378.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, 14 pages.

* cited by examiner

US 11,837,343 B2

IDENTIFYING REPETITIVE PORTIONS OF CLINICAL NOTES AND GENERATING SUMMARIES PERTINENT TO TREATMENT OF A PATIENT BASED ON THE IDENTIFIED REPETITIVE PORTIONS

BACKGROUND

The present application relates generally to an improved data processing apparatus and method and more specifically to mechanisms for identifying repetitive portions of clinical notes and generating summaries pertinent to treatment of a patient based on the identified repetitive portions.

An electronic health record (EHR) or electronic medical record (EMR) is the systematized collection of patient and population electronically-stored health information in a digital format. These records can be shared across different health care settings. Records are shared through network-connected, enterprise-wide information systems or other information networks and exchanges. EMRs may include a range of data, including demographics, social history, medical history, medication and allergies, immunization status, laboratory test results, radiology images, vital signs, personal statistics like age and weight, and billing information.

EMR systems are designed to store data accurately and to capture the state of a patient across time. It eliminates the need to track down a patient's previous paper medical records and assists in ensuring data is accurate and legible. It can reduce risk of data replication as there is only one modifiable file, which means the file is more likely up to date, and decreases risk of lost paperwork. Due to the digital information being searchable and in a single file, EMRs are more effective when extracting medical data for the examination of possible trends and long term changes in a patient. Population-based studies of medical records may also be facilitated by the widespread adoption of EMRs.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a repetitive portion identification and weighting engine. The method comprises training a machine learning model for weighting repetitive portions of patient electronic medical records (EMRs). The method further comprises applying, by a repetitive portion identification component executing within the repetitive portion identification and weighting engine, a plurality of templates to clinical notes of a patient EMR to identify one or more candidate portions that match at least one of the plurality of templates. The method further comprises performing, by a content analysis component executing within the repetitive portion identification and weighting engine, content analysis on the one or more candidate portions to determine whether each given candidate portion is relevant. The method further comprises assigning, by a weighting component executing within the repetitive portion identification and weighting engine, a relative weight to each given candidate portion based on relevance. The method further comprises generating, by a cognitive summary graphical user interface (GUI) generation component executing within the repetitive portion identification and weighting engine, cognitive summary reflecting at least a subset of the one or more candidate portions of the patient EMR. The method further comprises outputting the cognitive summary in a GUI to a user.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
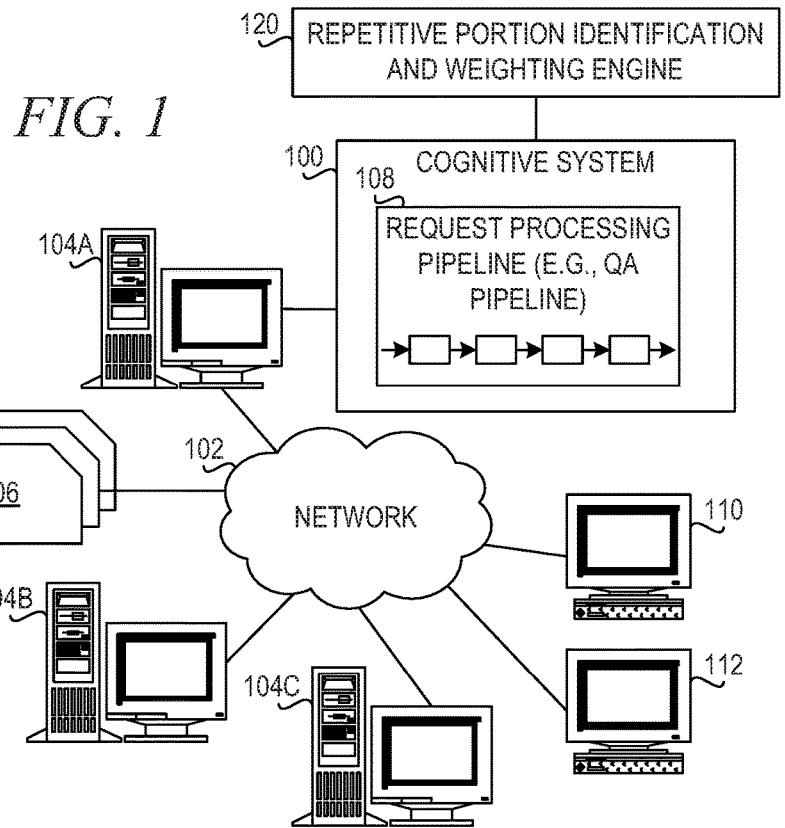
FIG. 1 depicts a schematic diagram of one illustrative embodiment of a cognitive healthcare system in a computer network.

Many times when a doctor is documenting an encounter with a patient, the doctor, in entering a clinical note into the patient record, may repeat portions of previous notes that may or may not be relevant to the current encounter. Moreover, for some kinds of repetitious information, repetition does not in fact indicate less accuracy or importance but, rather, routine important elements of clinical notes, e.g., temperature and blood pressure readings, particular laboratory results, etc. Thus, discriminating between irrelevant repetitive information and important repetitive information is context-dependent and difficult for automated systems to accomplish.

The illustrative embodiments provide a mechanism for identifying and evaluating repetitive content in clinical notes to determine their relative importance in conveying information to a medical professional, such as a doctor, about the patient's condition and/or treatment in a summary view of the patient's electronic medical record (EMR) via a cognitive system. That is, when providing a cognitive system that summarizes the most relevant portions of a patient's EMR for use by a doctor, the mechanism of the illustrative embodiments is able to discern (1) what portions of a clinical note are repetitive of other clinical notes or portions of the EMR; (2) the nature of the information conveyed in the repetitive portion relative to the treatment of the patient as a whole and/or the particular encounter for which the clinical note was generated; and, (3) based on the nature of the information conveyed, whether that repetitive portion should be weighted higher or lower than other portions of the EMR when generating a summary of the relevant portions of the EMR.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
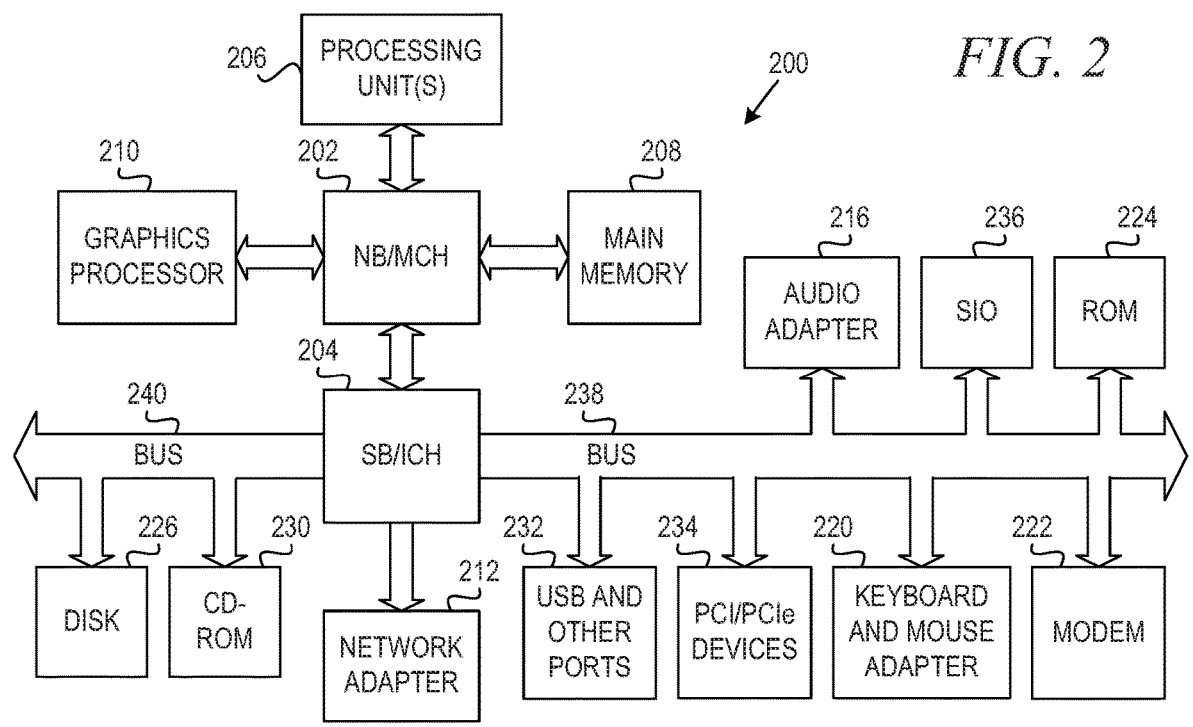
FIG. 2 is a block diagram of an example data processing system in which aspects of the illustrative embodiments are implemented.
Figure 3:
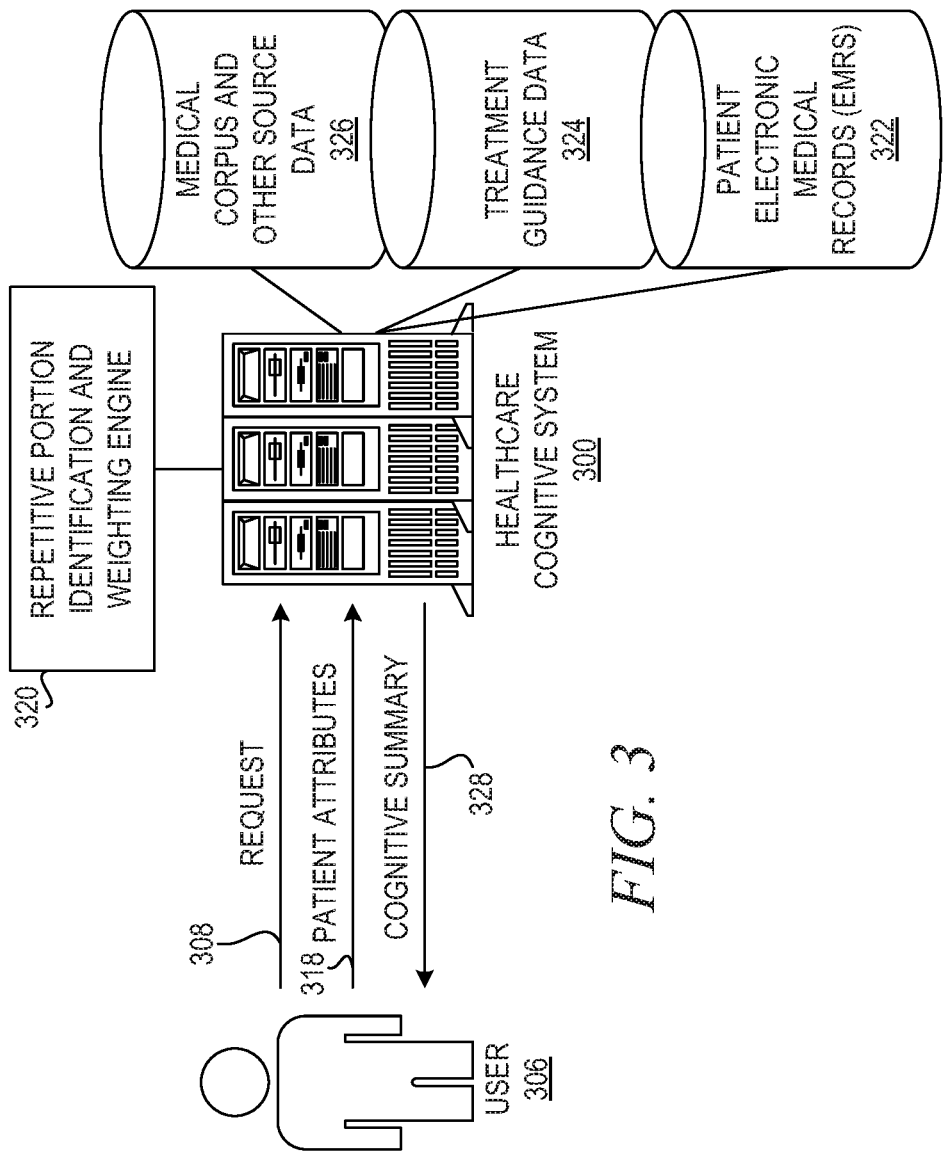
FIG. 3 is an example diagram illustrating an interaction of elements of a healthcare cognitive system in accordance with one illustrative embodiment.

As noted above, the present invention provides mechanisms for graphical presentation of relevant information from electronic medical records. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. These corpora may include, but are not limited to, EMR data. The cognitive system may determine what portions of a clinical note are repetitive of other clinical notes or portions of the EMR, the nature of the information conveyed in the repetitive portion relative to the treatment of the patient as a whole and/or the particular encounter for which the clinical note was generated, and based on the nature of the information conveyed, whether that repetitive portion should be weighted higher or lower than other portions of the EMR when generating a summary of the relevant portions of the EMR.

As will be discussed in greater detail hereafter, the illustrative embodiments may be integrated in, augment, and extend the functionality of these QA pipeline, or request processing pipeline, mechanisms of a healthcare cognitive system with regard to an electronic medical record completeness and data quality assessment mechanism.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, New York, which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate responses to generate ranked listing of candidate responses, which may then be presented to the user that submitted the input request, e.g., a user of client computing device 110, or from which a final response is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a repetitive portion identification and weighting engine 120 for identifying repetitive portions of clinical notes or portions of a patient EMR, analyzing the content of the repetitive portions, and weighting or ranking the repetitive portions for inclusion in a summary of the relevant portions of the patient EMR.

Repetitive portion identification and weighting engine 120 is provided with templates or patterns of natural language content that typically exist in a clinical note. In some embodiments, these templates or patterns for a particular doctor or medical professional may be learned over time through analysis of his or her particular style of entering information into clinical notes of the patient EMRs. Repetitive portion identification and weighting engine 120 applies these templates/patterns to clinical notes of a patient EMR to identify portions of the clinical notes that match the templates/patterns and, thus, are candidates for classification as repetitive content. Repetitive portion identification and weighting engine 120 compares content of the candidate portions to the patient's overall current medical condition and the treatments prescribed to determine whether the repetitive portion content is pertinent to the patient's overall medical condition or the reason for the patient's scheduled encounter with the medical professional. Repetitive portion identification and weighting engine 120 weights or ranks the candidate repetitive portions based on the degree of relevance to the context of the encounter.

It should be appreciated that the repetitive content may be a portion of a clinical note such that the evaluation of a single clinical note may result in different portions having different relative weights. For example, a doctor may copy an old entry in the patient's EMR and then add additional content pertinent to the particular encounter. As a result, repetitive portion identification and weighting engine 120 may assign a higher weight to the new content that was added and assign a lower weight to the repetitive content.

The relative weights of portions of clinical notes may be used to identify which portions of clinical notes should be reflected in summarizations generated by the cognitive system, which provides a summary graphical user interface (GUI) or dashboard representation of the patient's EMR that is directed to the current medical condition and treatment of the patient, anticipates the questions that the medical professional is likely to ask about the patient, and provides the corresponding answers from the patient's EMR. The mechanisms of the illustrative embodiments provide underlying functionality to facilitate the presentation of this summary representation by identifying which portions of the clinical notes are more important than others that are considered repetitious.

The key aspects of the clinical notes can be augmented with additional features based on external resources, such as unlabeled data and external rule-based systems related to similar data. Because manual labeling is very tedious and expensive, the availability of labeled data and manually constructed features is limited. The illustrative embodiments expand the training data features by automatically discovering correlations between the training data and features in the external resources. Hence, aspects related to the patient from social media streams or aspects related to the patient diagnosis from a research corpus of data are identified and weighted to inform the medical professional and to keep the clinical notes augmented and up-to-date with the patient's latest context. The additional features may lead the medical professional to ask clarification questions, and comments added to the automatically identified features may trigger the increase of weights of those features in proportion to the number of patients that feature was pursued for.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. The cognitive summary 328 may be presented in a ranked ordering with associated supporting evidence, obtained from the patient attributes 318 and data sources 322-326, indicating the reasoning as to why portions of EMR data 322 are being provided.

Note that EMR data 322 or data presented to the user may come from home readings or measurements that the patient makes available and are collected into EMR data 322.

In accordance with the illustrative embodiments herein, the healthcare cognitive system 300 is augmented to include a repetitive portion identification and weighting engine 320 for identifying repetitive portions of clinical notes or portions of a patient EMR, analyzing the content of the repetitive portions, and weighting or ranking the repetitive portions for inclusion in a summary of the relevant portions of the patient EMR. The repetitive portion identification and weighting engine 320 is described in further detail below.

Figure 4:
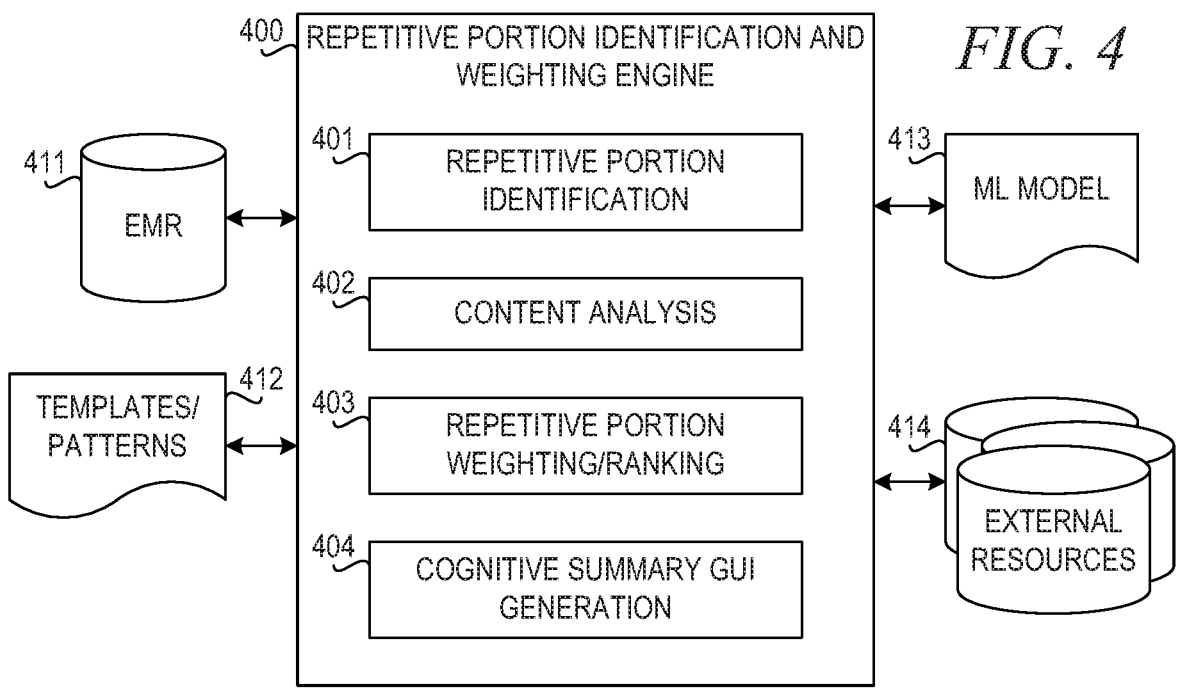
FIG. 4 is a block diagram of a repetitive portion identification and weighting engine in accordance with an illustrative embodiment.

FIG. 4 is a block diagram of a repetitive portion identification and weighting engine in accordance with an illustrative embodiment. Repetitive portion identification and weighting engine 400 comprises repetitive portion identification component 401, content analysis component 402, repetitive portion weighting/ranking component 403, and competitive summary graphical user interface (GUI) generation component 404. Repetitive portion identification and weighting engine 400 receives electronic medical record 411 containing clinical notes for a given patient.

Repetitive portion identification and weighting engine 400 also receives templates/patterns 412 of natural language content that typically exist in a clinical note. In some embodiments, templates/patterns 412 may be for a particular doctor or medical professional and learned over time through analysis of his or her particular style of entry of information into clinical notes of patient EMRs.

Repetitive portion identification component 401 applies templates/patterns 412 to clinical notes in patient EMR 411 to identify portions of the clinical notes that match templates/patterns within a given tolerance. For example, repetitive portion identification component 401 may use fuzzy matching to match portions of clinical notes in EMR 411 to templates/patterns 412. Any matching portions of EMR 411 are thus candidates for classification as repetitive content, indicating a relatively lower level of importance for inclusion in summarization. Repetitive portion identification component 401 may identify candidate repetitive portions using machine learning model 413.

Content analysis component 402 compares the subject matter or content of the candidate repetitive portions to content that is important to a patient's overall current medical condition (e.g., the diseases with which the patient has been diagnosed) and the treatments prescribed (e.g., particular medications, etc.) to determine if the repetitive content is pertinent to the patient's overall medical condition. In addition, content analysis component 402 performs a similar comparison with regard to the reason for the patient's current scheduled encounter with the medical professional. For example, the patient may have been diagnosed with Type 2 diabetes, but the current encounter is to look at a sprained ankle. In one embodiment, content analysis component 402 may use machine learning model 413 to compare the candidate repetitive portions to the patient's overall condition or reason for the encounter. Repetitive portion weighting/ranking component 403 assigns weights to the candidate repetitive portions based on the degree of relevance of the repetitive content to these contexts. Repetitive portion weighting/ranking component 403 may adjust the weights higher or lower based on trained machine learning model 413.

It should be appreciated that the repetitive content may be a portion of a clinical note such that the evaluation of a single clinical note may result in different portions having different relative weights. For example, a doctor may copy an old entry in the patient's EMR and then add additional content to the particular encounter. As a result, repetitive portion weighting/ranking component 403 will weight more highly the new content that was added and less highly the repetitive content.

Cognitive summary graphical user interface (GUI) generation component 404 generates a GUI for a cognitive summary of the patient EMR 411 for the medical professional's encounter with the patient. Cognitive summary GUI generation component 404 uses the relative weightings of the portions of the clinical notes in EMR 411 to identify which portions of the clinical notes should be reflected in the cognitive summary GUI. The cognitive system provides the summary GUI or dashboard representation of the patient's EMR, which is directed to the current medical condition and treatment of the patient 411, anticipates the questions that the doctor is likely to ask about the patient, and provides the corresponding answers to the questions from the patient's EMR 411. Repetitive portion identification and weighting engine 400 provides underlying functionality to facilitate the presentation of this cognitive summary representation by identifying which portions of the clinical notes are more important than others that are considered repetitive.

The key aspects of the clinical notes can be augmented with additional features based on external resources 414, such as unlabeled data and external rule-based systems related to similar data. Because manual labeling is very tedious and expensive, the availability of labeled data and manually constructed features is limited. One illustrative embodiment expands the training data features by automatically discovering their correlations with features in the external resources 414. Hence, aspects related to the patient from social media streams or aspects related to the patient diagnosis from research corpus of data are identified and weighted to inform the medical professional to ask clarifying questions, and comments added to the automatically identified features will trigger the increase of the weight of those features in proportion to the number of patients that feature was pursued for.

Figure 5:
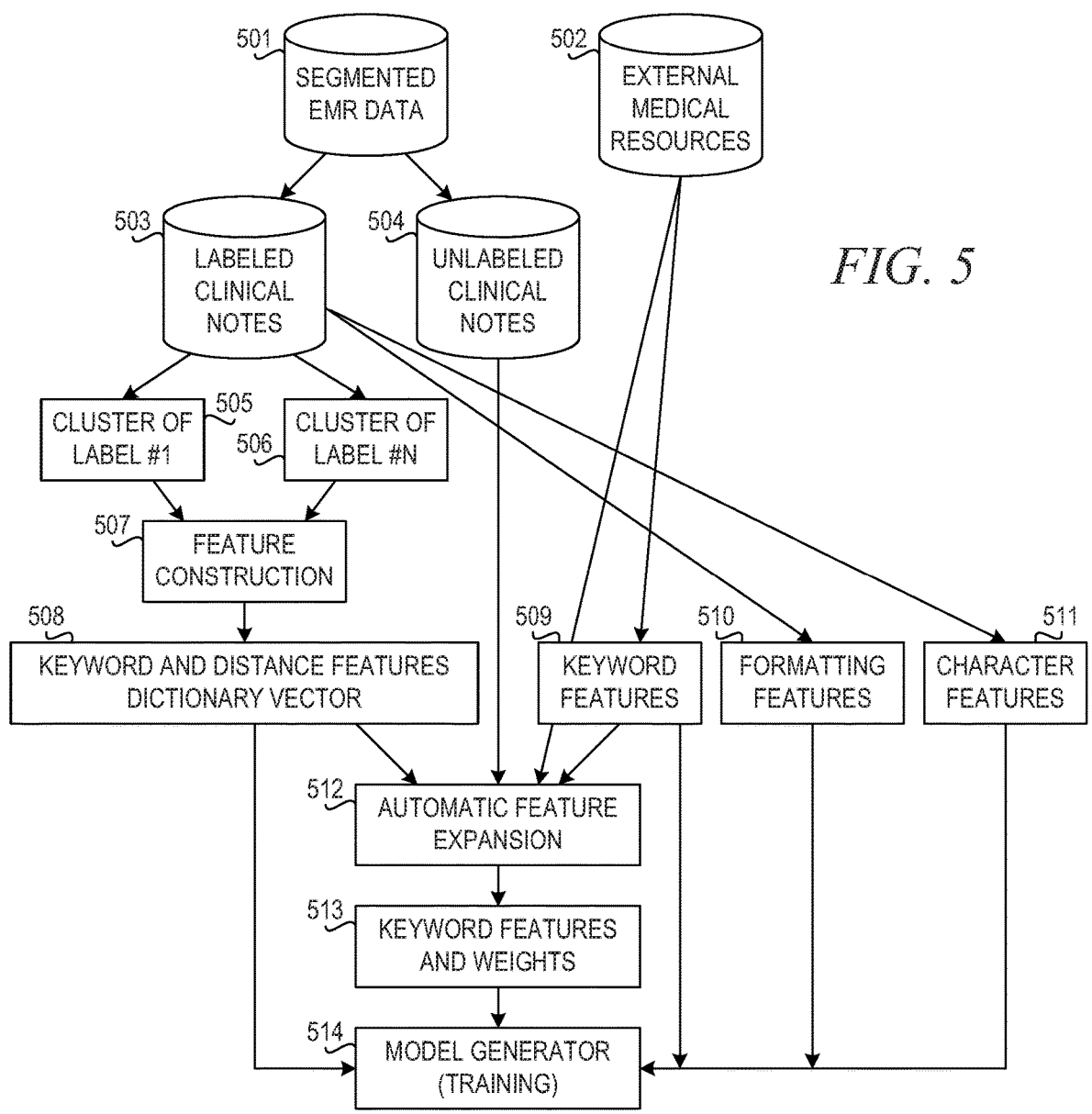
FIG. 5 illustrates operation of augmenting key aspects of clinical notes with additional features based on external resources in accordance with an illustrative embodiment.

FIG. 5 illustrates operation of augmenting key aspects of clinical notes with additional features based on external resources in accordance with an illustrative embodiment. Segmented EMR data 501 is divided into labeled clinical notes 503 and unlabeled clinical notes 504. Labeled clinical notes 503 can be clustered into cluster of label #1 505 to cluster of label #N 506, which are provided to feature construction 507, formatting features 510, and character features 511. Feature construction 507 generates keyword and distance features dictionary vector 508.

External medical resources 502 provide features to keyword features 509 and automatic feature expansion 512, which also receives keyword and distance features dictionary vector 508, unlabeled clinical notes 504, and keyword features 509. Automatic feature expansion 512 generates keyword features and weights 513, which are provided to model generator 514. Keyword and distance features dictionary vector 508, keyword features 509, formatting features 510, and characters features 511 are also provided to model generator 514, which trains a machine learning model for augmenting key aspects of clinical notes with additional features based on external medical resources 502.

Figure 6:
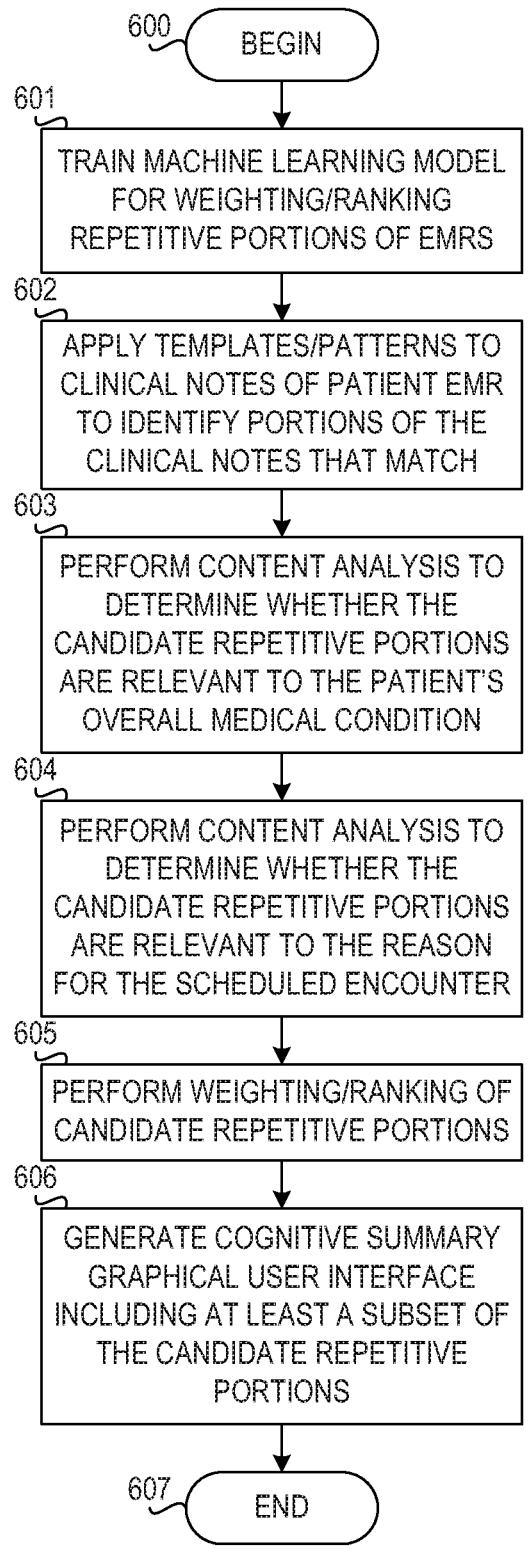
FIG. 6 is a flowchart illustrating operation of a mechanism for repetitive portion identification and weighting in accordance with an illustrative embodiment.

FIG. 6 is a flowchart illustrating operation of a mechanism for repetitive portion identification and weighting in accordance with an illustrative embodiment. Operation begins (block 600), and the mechanism trains a machine learning model for weighting/ranking repetitive portions of electronic medical records (EMRs) (block 601). The mechanism applies templates/patterns to clinical notes of patient EMR to identify portions of the clinical notes that match (block 602).

The mechanism performs content analysis to determine whether the candidate repetitive portions are relevant to the patient's overall medical condition (block 603). The mechanism also performs content analysis to determine whether the candidate repetitive portions are relevant to the reason for the scheduled encounter (block 604). The mechanism performs weighting/ranking of the candidate repetitive portions based on the content analysis (block 605). Then, the mechanism generates a cognitive summary graphical user interface (GUI) including at least a subset of the candidate repetitive portions (block 606). Thereafter, operation ends (block 607).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a repetitive portion identification and weighting engine, the method comprising:

training a machine learning model for weighting repetitive portions of patient electronic medical records (EMRs), wherein training the machine learning model comprises:

dividing the patient EMRs into labeled clinical notes and unlabeled clinical notes;

performing feature construction on clusters of labels from the labeled clinical notes to form labeled keyword features;

extracting formatting features and character features from the labeled clinical notes;

performing automatic feature expansion based on the labeled keyword features, the unlabeled clinical notes, and external keyword features from external medical resources to generate training keyword features and weights; and training the machine learning model based on the training keyword features and weights, the labeled keyword features, the external keyword features, the formatting features, and the characters features to output weights for repetitive portions of patient EMRs, wherein the weights indicate a relevance of corresponding repetitive portions;

applying, by a repetitive portion identification component executing within the repetitive portion identification and weighting engine, a plurality of templates to clinical notes of a patient EMR to identify one or more candidate portions that match at least one of the plurality of templates for classification as repetitive content;

performing, by a content analysis component executing within the repetitive portion identification and weighting engine, content analysis on the one or more candidate portions to determine whether each given candidate portion is relevant using the trained machine learning model;

assigning, by a weighting component executing within the repetitive portion identification and weighting engine, a relative weight to each given candidate portion based on relevance using the trained machine learning model;

generating, by a cognitive summary graphical user interface (GUI) generation component executing within the repetitive portion identification and weighting engine, a cognitive summary based on the relative weights of the one or more candidate portions of the patient EMR; and outputting, by the cognitive summary GUI generation component, the cognitive summary in a GUI to a user.

2. The method of claim 1, wherein performing the content analysis on the one or more candidate portions comprises determining whether each given candidate portion is relevant to the patient's overall medical condition.

3. The method of claim 1, wherein performing the content analysis on the one or more candidate portions comprises determining whether each given candidate portion is relevant to a reason for the patient's scheduled encounter with a medical professional.

4. The method of claim 1, wherein the external resources include social media streams or a research corpus.

5. A computer program product comprising a non-transitory computer readable storage medium having a computer readable program stored therein, wherein the computer readable program, when executed on a computing device, causes the computing device to implement a repetitive portion identification and weighting engine, wherein the computer readable program causes the computing device to:

train a machine learning model for weighting repetitive portions of patient electronic medical records (EMRs), wherein training the machine learning model comprises:

dividing the patient EMRs into labeled clinical notes and unlabeled clinical notes;

performing feature construction on clusters of labels from the labeled clinical notes to form labeled keyword features;

extracting formatting features and character features from the labeled clinical notes;

performing automatic feature expansion based on the labeled keyword features, the unlabeled clinical notes, and external keyword features from external medical resources to generate training keyword features and weights; and training the machine learning model based on the training keyword features and weights, the labeled keyword features, the external keyword features, the formatting features, and the characters features to output weights for repetitive portions of patient EMRs, wherein the weights indicate a relevance of corresponding repetitive portions;

apply, by a repetitive portion identification component executing within the repetitive portion identification and weighting engine, a plurality of templates to clinical notes of a patient EMR to identify one or more candidate portions that match at least one of the plurality of templates for classification as repetitive content;

perform, by a content analysis component executing within the repetitive portion identification and weighting engine, content analysis on the one or more candidate portions to determine whether each given candidate portion is relevant using the trained machine learning model;

assign, by a weighting component executing within the repetitive portion identification and weighting engine, a relative weight to each given candidate portion based on relevance using the trained machine learning model;

generate, by a cognitive summary graphical user interface (GUI) generation component executing within the repetitive portion identification and weighting engine, a cognitive summary based on the relative weights of the one or more candidate portions of the patient EMR; and output, by the cognitive summary GUI generation component, the cognitive summary in a GUI to a user.

6. The computer program product of claim 5, wherein performing the content analysis on the one or more candidate portions comprises determining whether each given candidate portion is relevant to the patient's overall medical condition.

7. The computer program product of claim 5, wherein performing the content analysis on the one or more candidate portions comprises determining whether each given candidate portion is relevant to a reason for the patient's scheduled encounter with a medical professional.

8. The computer program product of claim 5, wherein the external resources include social media streams or a research corpus.

9. An apparatus comprising:

at least one processor; and a memory coupled to the at least one processor, wherein the memory comprises instructions which, when executed by the at least one processor, cause the at least one processor to implement a repetitive portion identification and weighting engine, wherein the instructions cause the at least one processor to:

train a machine learning model for weighting repetitive portions of patient electronic medical records (EMRs), wherein training the machine learning model comprises:

dividing the patient EMRs into labeled clinical notes and unlabeled clinical notes;

performing feature construction on clusters of labels from the labeled clinical notes to form labeled keyword features;

extracting formatting features and character features from the labeled clinical notes;

performing automatic feature expansion based on the labeled keyword features, the unlabeled clinical notes, and external keyword features from external medical resources to generate training keyword features and weights; and training the machine learning model based on the training keyword features and weights, the labeled keyword features, the external keyword features, the formatting features, and the characters features to output weights for repetitive portions of patient EMRs, wherein the weights indicate a relevance of corresponding repetitive portions;

apply, by a repetitive portion identification component executing within the repetitive portion identification and weighting engine, a plurality of templates to clinical notes of a patient EMR to identify one or more candidate portions that match at least one of the plurality of templates for classification as repetitive content;

perform, by a content analysis component executing within the repetitive portion identification and weighting engine, content analysis on the one or more candidate portions to determine whether each given candidate portion is relevant using the trained machine learning model;

assign, by a weighting component executing within the repetitive portion identification and weighting engine, a relative weight to each given candidate portion based on relevance using the trained machine learning model;

generate, by a cognitive summary graphical user interface (GUI) generation component executing within the repetitive portion identification and weighting engine, a cognitive summary based on the relative weights of the one or more candidate portions of the patient EMR; and output, by the cognitive summary GUI generation component, the cognitive summary in a GUI to a user.

10. The apparatus of claim 9, wherein performing the content analysis on the one or more candidate portions comprises determining whether each given candidate portion is relevant to the patient's overall medical condition.

11. The apparatus of claim 9, wherein performing the content analysis on the one or more candidate portions comprises determining whether each given candidate portion is relevant to a reason for the patient's scheduled encounter with a medical professional.

12. The apparatus of claim 9, wherein the external resources include social media streams or a research corpus.

13. The method of claim 1, wherein the plurality of templates are learned over time through analysis of a medical professional's particular style of entering information into clinical notes of patient EMRs.

14. The method of claim 1, wherein the cognitive summary graphical user interface (GUI) generation component anticipates questions that the medical professional is likely to ask about the patient and provides corresponding answers to the questions from the patient EMR.

15. The computer program product of claim 5, wherein the plurality of templates are learned over time through analysis of a medical professional's particular style of entering information into clinical notes of patient EMRs.

16. The computer program product of claim 5, wherein the cognitive summary graphical user interface (GUI) generation component anticipates questions that the medical professional is likely to ask about the patient and provides corresponding answers to the questions from the patient EMR.

17. The apparatus of claim 9, wherein the plurality of templates are learned over time through analysis of a medical professional's particular style of entering information into clinical notes of patient EMRs.

18. The apparatus of claim 9, wherein the cognitive summary graphical user interface (GUI) generation component anticipates questions that the medical professional is likely to ask about the patient and provides corresponding answers to the questions from the patient EMR.

* * * * *